United States Patent [19]

Iuchi

[11] Patent Number: 4,647,319
[45] Date of Patent: Mar. 3, 1987

[54] METHOD FOR QUANTITATIVELY DETECTING THE DECARBURIZATION REACTION IN THE PRODUCTION PROCESS OF AN ELECTRICAL STEEL SHEET

[75] Inventor: Tohru Iuchi, Kawasaki, Japan

[73] Assignee: Nippon Steel Corporation, Tokyo, Japan

[21] Appl. No.: 681,629

[22] Filed: Dec. 14, 1984

[30] Foreign Application Priority Data

Dec. 20, 1983 [JP] Japan ................................ 58-240678
Jan. 20, 1984 [JP] Japan .................................. 59-9192

[51] Int. Cl.$^4$ ............................................. C21D 11/00
[52] U.S. Cl. ........................................ 148/128; 266/90
[58] Field of Search ........................ 148/128, 129, 100; 266/99, 80, 90, 96, 100

[56] References Cited

U.S. PATENT DOCUMENTS 2,886,478  5/1959  Beard .................................. 148/128
2,914,434 11/1959  Snavely ............................... 148/128
3,463,631  8/1969  Vaysseire et al. ..................... 266/99
4,288,062  9/1981  Gupta et al. .......................... 266/80

FOREIGN PATENT DOCUMENTS 58-55530  4/1983  Japan .
58-43691  9/1983  Japan .

OTHER PUBLICATIONS

"Steel Handbook IV, 3rd Edition", Edited by the Japan Institute for Iron and Steel, p. 561.

Primary Examiner—Melvyn J. Andrews
Assistant Examiner—S. Kastler
Attorney, Agent, or Firm—Kenyon & Kenyon

[57] ABSTRACT

The decarburization reaction which occurs in the production of an electrical steel sheet is quantitatively detected by passing an electromagnetic wave beam into the vicinity of the sheet, which is positioned in an annealing furnace, and then measuring the absorption amount of the electromagnetic wave beam, which is absorbed by water vapor in the vicinity of the steel sheet and/or by CO gas formed due to the reaction between the water vapor and the steel sheet.

10 Claims, 5 Drawing Figures

METHOD FOR QUANTITATIVELY DETECTING THE DECARBURIZATION REACTION IN THE PRODUCTION PROCESS OF AN ELECTRICAL STEEL SHEET

BACKGROUND OF THE INVENTION

1. Field of the Invention

The present invention relates to a method for quantitatively detecting the decarburization reaction occurring in an annealing furnace during the production of an electrical steel sheet. More particularly, the present invention relates to a method for in situ detection of the decarburization reaction which occurs in an annealing furnace.

2. Description of the Related Art

An electrical steel sheet is used for the core of electrical machinery and devices. Electrical steel sheets are largely classified into two types, i.e., a non-oriented electrical steel sheet which is produced by utilizing primary recrystallization and normal grain growth and a grain-oriented electrical steel sheet which is produced by utilizing a phenomenon in which crystal grains having a particular crystal orientation, e.g., the orientation expressed by the Miller index as $\{110\}<001>$, are caused to grow abnormally, this abnormal growth being referred to as secondary recrystallization.

Carbon is one of the impurities of a non-oriented electrical steel sheet and is removed or decarburized during its production to as low a level as possible since the carbon remaining in the final product impairs the magnetic properties of the product and, with the lapse of time, the magnetic properties of the core in which the product is used gradually deteriorate. This deterioration is referred to as a magnetic aging phenomenon.

The carbon content of silicon steels can be decreased in the molten-steel processing stage including steelmaking and the pretreatment of molten steel. If it is attempted to attain in the molten-steel processing stage a low carbon content which is not detrimental to the magnetic properties, a sophisticated operation technique which is indispensable for attaining the desired carbon level renders the production efficiency at steelmaking very low. Therefore, some carbon usually remains in the molten-steel processing stage and is removed or decarburized at a later stage. This decarburization is usually carried out during the annealing stage, i.e., decaburization is attained together with primary recrystallization and normal grain growth during annealing.

In the production of a grain-oriented electrical steel sheet, a certain carbon content is necessary for realizing stable secondary recrystallization. Molten steel has, therefore, a carbon content of from approximately 0.02% to 0.06% so that such carbon content of a strip creates a condition for stable secondary recrystallization.

The necessity of controlling the carbon content in the range above has long been known in the pertinent technical field.

Japanese Unexamined Patent Publication No. 58-55530 discloses a representative method for controlling the carbon content. In the method disclosed in this publication, the product is obtained by the following processes: single pass cold-rolling of a hot-rolled strip or a multi pass of cold-rollings with intermediate annealing to obtain the final thickness of the product; decarburizing annealing in a wet hydrogen atmosphere; applying and then drying powder mainly composed of MgO; and subsequently annealing at a temperature exceeding 1100° C. The aims of this annealing carried out at the final production step are to generate secondary recrystallization and to form a ceramic insulating material mainly composed of $2MgO.SiO_2$ due to the reaction between $SiO_2$, which is formed on the sheet surface during the decarburizing-annealing step, and MgO, which is applied on the sheet surface. An aim of decarburizing-annealing is to reduce the carbon content of the steel sheet prior to secondary recrystallization annealing to as low as possible, usually 0.002% or less, thereby stably generating secondary recrystallization.

Conventionally, the decarburization of a hot-rolled steel sheet is carried out only in the decarburizing-annealing step. As is disclosed in Japanese Unexamined Patent Publication No. 58-5530 mentioned above, the optimum carbon amount for secondary recrystallization depends on the carbon amount in the cold-rolling step. Therefore, according to a recently employed decarburization method, decarburization is carried out in the annealing step of a hot-rolled strip or in the intermediate annealing step so as to provide such a complete decarburization as previously attained in the decarburizing annealing step.

In summary, no matter what kind of non-oriented or grain-oriented electrical steel sheet is to be produced decarburization is carried out by annealing.

Incidentally, decarburization proceeds, during the decarburizing-annealing step, according to the following reactions: $C(\text{in Fe-Si}) + H_2O \rightleftharpoons CO + H_2$. Since the amount of carbon in steel is great at the initial period of annealing, the amount of CO formed is great. If a considerable amount of CO is formed, the reaction mentioned above proceeds in the left direction or an oxide is formed on the surface of the steel sheet, with the result that the decarburization rate is retarded. In this case, it is necessary either to increase the $H_2O$ or to dilute the formed CO with a supplying gas medium in order to promote decarburization. In an annealing period where decarburization proceeds and the carbon amount in steel is thus decreased, the amount of formed CO becomes low. In this case, unless the $H_2O$ amount in the gas annealing atmosphere is decreased, an oxide of high order is formed on the surface of the steel sheet. It is accordingly necessary to detect the $H_2O$ and CO amounts in the annealing atmosphere and to control the annealing atmosphere depending upon the detected $H_2O$ and CO amounts. This control is effected by supplying gases into the annealing furnace or adjusting the dew point of the gas atmosphere of the annealing furnace. Such control is the strictest in the decarburizing-annealing step, which is carried out after the final cold-rolling step of production of a grain-oriented electrical steel sheet, as is described in detail hereinafter.

The principal aims of decarburizing-annealing are to cause primary recrystallization of the cold-rolled steel sheet and decarburization, as well as to form a silica-scale layer, i.e., an oxide film. The silica-scale layer formed in the decarburizing-annealing step exerts great influences on the formation of a primary film, i.e., a forstellite film which is formed at a later step than the decarburizing-annealing step. The formation of a silica-scale layer and its properties therefore play an important role in determining the power loss characteristics of the articles in which the grain-oriented electrical steel sheet is used.

The H₂O, which participates in the above-described decarburization reaction C+H₂O⇌CO+H₂ and which is brought into reaction with the carbon in steel, is the water vapor contained in the gas atmosphere of the annealing furnace. In the decarburizing-annealing step, decarburization by H₂O first occurs. If, however, the H₂O partial pressure is too high, a film of oxides, such as FeO, Fe₂O₃, and the like, is formed on the surface of the steel sheet and impedes the contact between the H₂O and C, thereby suppressing decarburization and hence impairing the magnetic properties.

The H₂O then reacts with the Si contained in the steel in a later half period of the decarburizing-annealing step and causes the formation of a silica-layer scale, i.e., a film of oxides, such as SiO₂, 2FeO.SiO₂, and the like, according to the following reactions:

If these reactions proceed to the extent of excessive oxidation, the adhesiveness of the film is impaired and the film thickness exceeds that of requisite primary film, resulting in a reduction in the space factor of a core and impairment of the film properties. Oxidation by the above reactions should be controlled to provide the oxide film with an amount and composition appropriate for forming a primary coating having an excellent quality since the amount and composition of the oxide film exerts an influence on the quality of glassy insulating film mainly composed of 2MgO.SiO₂ and referred to as the primary coating.

As is described above, both the decarburization reaction and the oxidation reaction for forming an oxide layer occur in the decarburizing-annealing step.

To attain compatible satisfactory decarburization and appropriate formation of the oxide layer, it is important that the gas atmosphere, dew point, time, and the like of decarburizing-annealing be delicately controlled.

Conventionally, the partial-pressure ratio $P_{H_2O}/P_{H_2}$ of the water vapor and hydrogen gas or the dew point of the gases of the annealing furnace is controlled, such as is disclosed in Japanese Examined Patent Publication No. 58-43,691. The partial-pressure ratio and the dew point are determined by measuring the proportion of water vapor to hydrogen prior to admitting the supply gases into the annealing furnace. Alternatively, as is described in "Steel Handbook IV, 3rd Edition", edited by the Japan Institute for Iron and Steel, page 561, a dew probe, in which the hygroscopic saturation characteristic of lithium chloride is employed, is attached to the annealing furnace, and the gas atmosphere of the furnace is sucked outside the furnace into the dew probe to measure the dew point. In this case, the gas atmosphere at a portion of the furnace interior is used to measure the dew point. The so-detected values are not considered to provide true information on decarburization and oxide-film formation since the partial-pressure ratio and dew point undoubtedly greatly vary spatially within the huge space of the annealing furnace.

By "true information", the inventor means the state of the gas atmosphere in the neighborhood of the steel sheet. The inventor understands the necessity of quantitatively recognizing decarburization including the formation of an oxide film and occurring due to reactions between the surface of the steel sheet and water vapor present in the vicinity of the surface.

Since conventional methods for measuring the dew point and the like involve points to be improved, conventional decarburization-controlling methods cannot be said to be satisfactory. That is, since an appropriate method for obtaining true information has not heretofore been provided, decarburization control not based on true information has been carried out previously.

SUMMARY OF THE INVENTION

The present inventor conceived the concept of utilizing an electromagnetic wave for measuring the dew point. The dew point measurement method involved in this concept is to pass an electromagnetic wave beam in the vicinity of an article in a furnace and measure the absorption of the electromagnetic wave by the water vapor within the furnace. By this process, the dew point in the vicinity of the article in the furnace can be measured. The above concept is applied in the process for producing an electrical steel sheet.

It is an object of the present invention to provide more useful information for the operation control of the decarburizing step of electrical steel sheet production than do conventional methods for measuring the gas atmosphere of an annealing furnace.

It is a specific object of the present invention to provide a method for measuring the concentration of water vapor in the vicinity of the surface of a steel sheet where the decarburization reaction occurs.

It is another specific object of the present invention to provide a method for simultaneously measuring in the vicinity of the surface of a steel sheet where decarburization occurs the concentration of water vapor and the concentration of CO gas, i.e., the reaction product.

It is a further specific object of the present invention to provide a method for measuring the partial pressures of CO gas and water vapor or the partial-pressure ratio $P_{H_2O}/P_{CO}$.

The concentration of water vapor and/or CO gas, the partial pressures of water vapor and CO gas, the partial-pressure ratio $P_{H_2O}/P_{CO}$, or the dew point corresponding to the concentration of water vapor in the immediate vicinity of a steel sheet in an annealing furnace is measured by utilizing the fact that when an electromagnetic wave beam having a particular wavelength exhibiting an absorption characteristic due to the water vapor and/or CO gas propagates in the furnace space, the absorption amount of the electromagnetic wave beam varies depending upon the amount of water vapor and CO gas.

DESCRIPTION OF THE PREFERRED EMBODIMENTS

Figure 1:
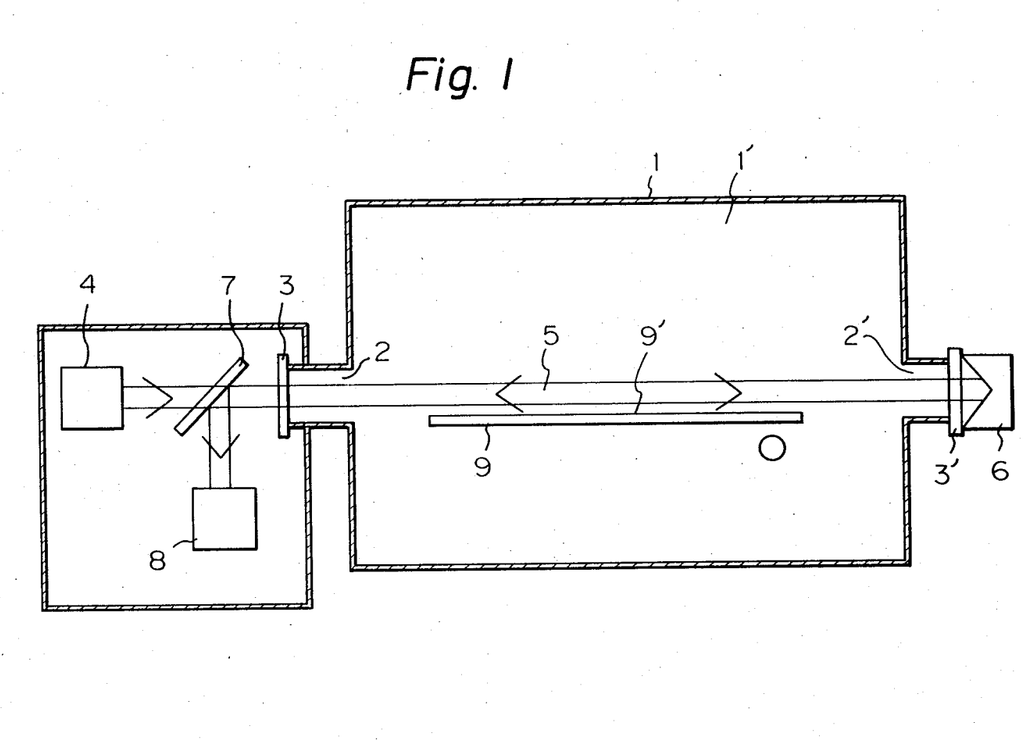
FIG. 1 is a drawing illustrating the measurement principle of the method according to the present invention.

Referring to FIG. 1, the fundamental elements of the present invention are shown.

A decarburizing-annealing furnace 1 is provided at both side walls 2, 2' with small apertures, which apertures are sealed by windows 3, 3' so as to prevent leakage of the gas atmosphere of the furnace interior. The windows 3, 3', which are transmissive to the electromagnetic wave, hereinafter referred to as electromagnetic wave transmissive windows 3, 3'. An electromagnetic wave beam 5 is emitted from the source 4, which is positioned, via the beam splitter 7, opposite the electromagnetic wave-transmissive window 3. The wavelength band of the electromagnetic wave from the light source includes one or more bands absorbed by water vapor, such as 1.39 μm, 1.84 μm, 2.7 μm, and 5.5–6.5 μm, and by CO gas, such as 4.6–4.7 μm. A detector 8 is positioned opposite the beam splitter 7. A reflection mirror 6, such as a Littrow reflector, is positioned outside the other electromagnetic wave-transmissive window 3'.

The electrical steel sheet 9 is positioned in the furnace interior 1' of the decarburizing-annealing furnace 1, and the surface 9' of the sheet is brought into an interface reaction with the water vapor in the furnace interior 1'.

The electromagnetic wave beam 5, e.g., an infrared ray beam, propagates so that it passes through the electromagnetic wave-transmissive window 3 and into the immediate vicinity of the surface 9'. The beam 5 is then reflected by the reflection mirror 6 and is again passed through the furnace interior 1'. The beam 5 is then reflected outside the furnace by the beam splitter 7 and is guided to the detector 8. The cross-sectional shape of the electromagnetic wave beam 5 can be optionally controlled by an optical technique but is preferably in the range of from 0.1 mm to 50 mm in diameter. The closer the distance between the beam 5 and the surface 9' of the electrical steel sheet, the more desirable is detection of the interface reaction. However, since there are practical problems, such as vibration of the electrical steel sheet 9 travelling in the decarburizing-annealing furnace 1, the distance between the beam 5 and the surface 9' of the electrical steel sheet 9 is preferably not less than 0.1 mm and not more than 100 mm. The wavelength of the electromagnetic wave is selected, in accordance with the gas or gases to be detected, to be 1.39 μm, 1.84 μm, 2.7 μm, or 5.5–6.5 μm in the case of water vapor and 4.6–4.7 μm in the case of CO gas. The intensity of the electromagnetic wave detected by the detector 8 varies depending upon the concentrations of water vapor and CO gas formed due to the decarburization reaction, and, therefore, the concentrations of water vapor and CO gas, the partial pressures of water vapor and CO gas, and/or the partial pressure ratio can be measured by the detector 8. This measurement is an in situ measurement of the furnace interior 1', where the decarburization reaction occurs.

The passage of the electromagnetic wave beam 5 across the surface 9' of the electrical steel sheet 9 may be in any direction. When the electromagnetic wave beam 5 passes along the width of the electrical steel sheet 9 in the furnace interior 1', the average values of water vapor and/or CO gas over the width can be obtained, that is, the components which participate in the interface reaction are detected by their average value at a particular section of the decarburizing-annealing furnace 1. This makes it possible to control the decarburization process and material qualities by a method which is completely different from the conventional control methods for a decarburizing-annealing furnace for the production of an electrical steel sheet. In addition, since the detection of the electromagnetic wave beam 5 can be carried out at a high speed, continuous measurement is always possible even when the electrical steel sheet 9 travels in the furnace interior 1' at a high speed.

The measurement principle according to the present invention is now described.

An infrared ray with a wavelength (λ) exhibiting an absorption characteristic to water vapor is expressed as having an intensity $I_w(Z)$ at a distance (Z). The intensity $I_w(Z)$ is expressed according to the Lambert-Beer low by the following general formula:

$$I_w(Z) = I_w(0) \exp(-\alpha_w \cdot n_w \cdot Z) \quad (1),$$

in which $I_w(0)$ = intensity at $Z=0$, i.e., the incidence intensity, $n_w$ = mole number of the water vapor per unit volume, and $\alpha_w$ = the attenuation constant of an infrared ray to water vapor.

When the distance from the light source 4 to the reflection mirror 6 is expressed by l, the propagation distance L becomes 2l (L=2l).

By substituting Z of the formula (1) with L, $$\frac{I_w(L)}{I_w(0)} = \exp(-\alpha_w \cdot n_w \cdot L) \quad (2)$$

Both sides of the formula (2) are changed logarithmic terms, and the $n_w$ of formula (2) is transposed to the left side.

$$n_w = \frac{1}{\alpha_w \cdot L} \ln \frac{I_w(L)}{I_w(0)} \quad (3)$$

Since $\alpha_w$ and L of the formula (3) are constants, the mole number of the water vapor per unit volume ($n_w$) is obtained from the ratio of the detected intensity ($I_{w(L)}$) to the incidence intensity ($I_{w(0)}$).

The furnace space shown in FIG. 1 is supposed to be an open system into which the moistened AX gas is supplied from outside to maintain a constant dew point therein and in which the pressure of the furnace interior is maintained at substantially 1 atmosphere. The relationship between the partial pressure of the water vapor $P_w$, the furnace volume V, the mole number of the water vapor $N_w$, and the temperature of the gas atmosphere in the furnace T(K) is established in the open system of the furnace space as follows:

$$P_w \cdot V = N_w \cdot R \cdot T \quad (4)$$

in which R is the gas constant.

Since the mole number of the water vapor per unit volume ($n_w$) is $N_w/V$, $P_w$ can be expressed as follows:

$$P_w = n_w \cdot R \cdot T \quad (5)$$

That is, when the mole number of the water vapor per unit volume ($n_w$) is measured according to the formula (3) and when T is determined by the furnace temperature, the partial pressure of the water vapor Pw in the furnace interior can be obtained by the formula (5).

Figure 2:
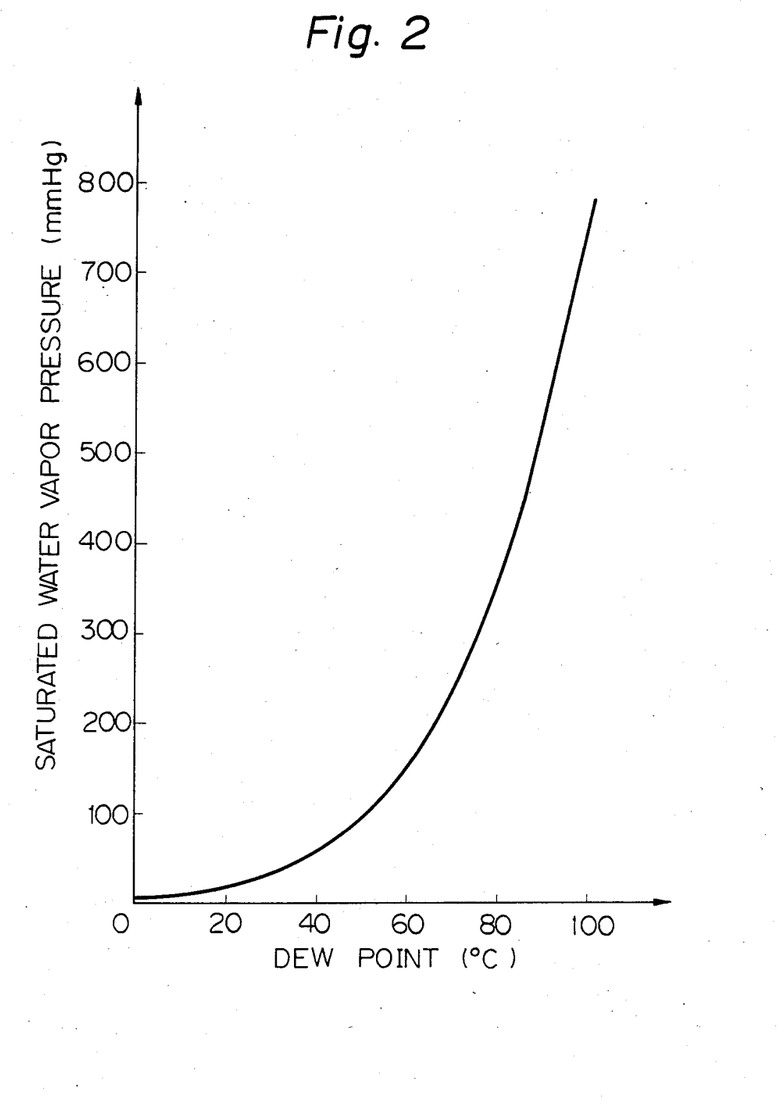
FIG. 2 is a graph showing the relationship between the dew point and the pressure of saturated water vapor.

In addition, since the relationship between the pressure of saturated water vapor corresponding to ($P_w$) and the dew point $t_w$ (°C.) has the uniqueness shown in FIG. 2, $P_w$ leads to the determination of the dew point $t_w$ (°C.).

Similarly, the mole number of the CO gas per unit volume of the furnace gas ($n_{CO}$) and the partial pressure of the CO gas ($P_{CO}$) are given by the following formulas:

$$n_{CO} = \frac{1}{a_{CO} \cdot L} \ln \frac{I_{CO(L)}}{I_{CO(0)}} \tag{6}$$

and $$P_{CO} = n_{CO} R. T \tag{7}$$

in which $I_{CO(0)}$ = the incidence intensity at Z=0 of an infrared ray, the wavelength of which is absorbed by the CO gas, $I_{CO(Z)}$ = the incidence intensity at a distance Z of an infrared ray, the wavelength of which is absorbed by the CO gas, and $a_{CO}$ = the attenuation constant of an infrared ray, the wavelength of which is absorbed by CO gas.

The formula (8) is obtained by the formulas (3) and (6), and the formula (9) is obtained by the formulas (5) and (7).

$$\frac{n_w}{n_{CO}} = \frac{a_{CO}}{a_w} \ln\left(\frac{I_{w(L)}}{I_{w(0)}}\right) / \ln\left(\frac{I_{CO(L)}}{I_{CO(0)}}\right) \tag{8}$$

$$\frac{P_w}{P_{CO}} = \frac{n_w}{n_{CO}} \tag{9}$$

The formula (9), in which the ratio of the partial pressure of water vapor, which causes the interface reaction, and the partial pressure of CO gas, which is the reaction product, are given, is a particulary appropriate formula to be used as an index of the reaction state of decarburization.

Figure 3:
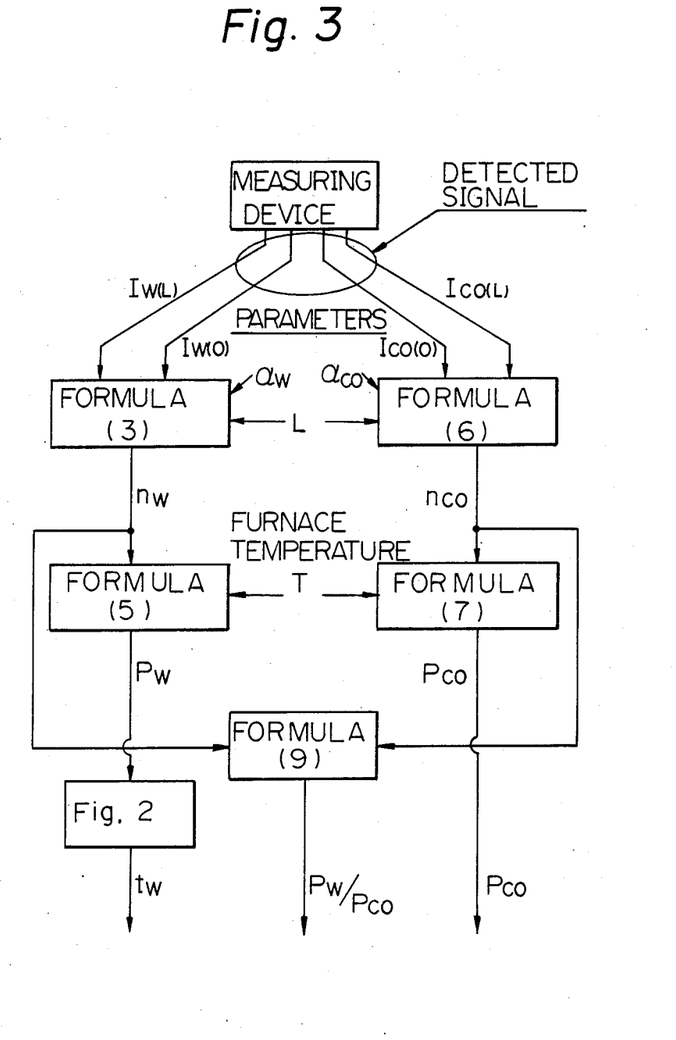
FIG. 3 is a block diagram of the measurement system according to the present invention.

Referring to FIG. 3, a block diagram of the measurement system is shown.

Figure 4:
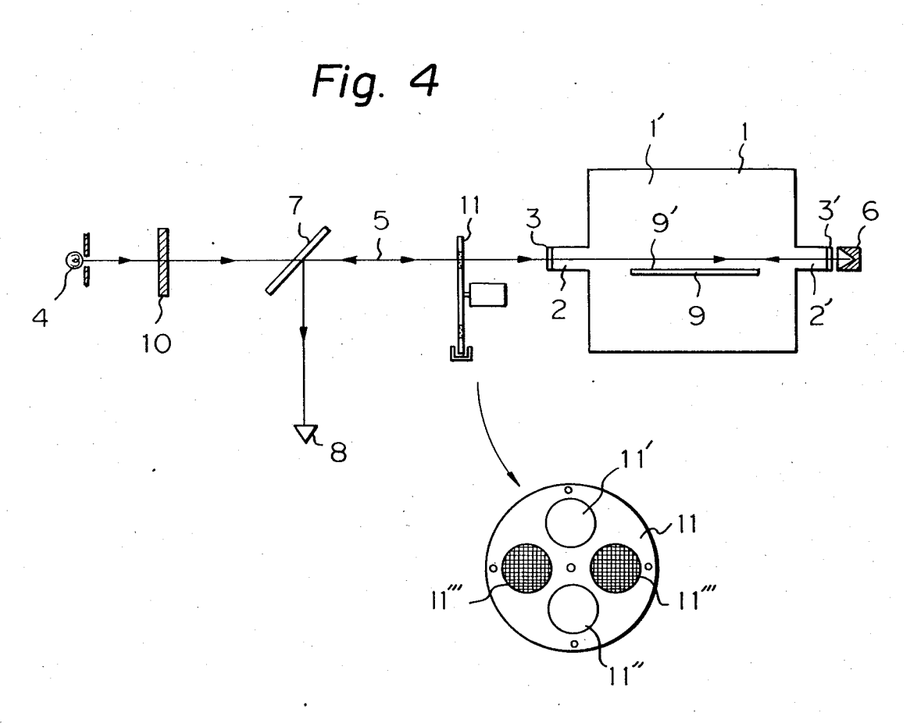
FIG. 4 is a drawing illustrating an embodiment according to the present invention.

Referring to FIG. 4, an embodiment, in which the present measurement principle is applied, is shown.

The electromagnetic wave beam 5 from the light source 4 has a wavelength band including the wavelength λ exhibiting the property of absorption by water vapor. Only this wavelength λ is passed through the filter 10. The electromagnetic wave beam 5 passed through the filter 10 arrives first at the beam splitter 7 and then at the rotary sector 11. The rotary sector 11 includes completely transmissive window 11', a total-reflection mirror 11", and a total-absorption surface 11'''. When the completely transmissive window 11' is positioned across the optical path of the electromagnetic wave beam 5 during the rotation of the rotary section 11, the beam 5 is emitted into and propagates in the furnace interior 1' and is reflected by the reflection mirror 6 along the previous optical path. The electromagnetic wave beam 5 is then reflected by the beam splitter 7 and enters the detector 8. The signal so detected by the detector 8 is expressed by $I_1$.

When the total-reflection mirror 11" is positioned across the optical path of the electromagnetic wave beam 5, total reflection of the beam 5 occurs there. The reflected beam 5 is reflected by the beam splitter 7 and then enters the detector 8, which detects the signal $I_2$.

When the total-absorption surface 11''' is positioned across the optical path, the signal which is reflected by the surface 11''' and is then detected by the detector 8 is deemed to be zero level and is expressed by $I_3$.

The above-described signals can be described as follows:

$$I_1 = k_1 I_\lambda(0) \exp(-a_n' Z_0 - a_n L) + I_b \tag{10}$$

$$I_2 = k_2 I_\lambda(0) \exp(-a_n' Z_0) + I_b \tag{11}$$

$$I_3 = I_b \tag{12}$$

The above $k_1$ and $k_2$ are constant coefficients in which the reflectivity of mirrors and geometrical constants of the optical system are included. The above n' is the optical distance from the rotary section 11 via the beam splitter 7 to the detector 8. The above $I_b$ is a detected noise value including the noise from the ambient background color.

$(I_1 - I_3)/(I_2 - I_3)$ is obtained from the following formulas (10)–(12):

$$\frac{I_1 - I_3}{I_2 - I_3} = \frac{k_1}{k_2} \exp(-a_n L) \tag{13}$$

The formula (14) is obtained from the following formula (13):

$$n = -\frac{1}{a \cdot L} \ln\left(k \frac{I_1 - I_3}{I_2 - I_3}\right), \tag{14}$$

in which $k = k_2/k_1$ = constant.

The mole number (n) of the water vapor per unit volume of the furnace interior (gas) is thus obtained from the formula (14).

A computing system connected to the detector 8 can perform the calculations as described above following the procedure shown in FIG. 2 and can readily give the value of "n".

The method for measuring water vapor is described with reference to FIG. 4. The method for measuring CO gas can be carried out similarly. Alternatively, both water vapor and CO gas can be measured simultaneously, provided that a beam having a wavelength absorbed by water vapor and a beam having a wavelength absorbed by CO gas propagate along the same optical path.

The present invention is now explained by way of examples.

EXAMPLE 1

Water vapor was measured in this example by using the embodiment shown in FIG. 4.

A tungsten-halogen lamp was used as the light source 4. An interference filter having a wavelength λ of 1.39 μm and a half-width Δλ of 0.15 μm was used as the filter 10. The electromagnetic wave beam 5 had a diameter of 3 mm and propagated over the surface 9' of the steel sheet at a distance of 10 mm from the surface 9'. A germanium (Ge) infrared ray sensor was used as the detector 8.

The furnace interior 1' was an open system and was maintained at 820° C. in terms of the temperature of the gas atmosphere. A constant amount of $N_2$ gas containing water vapor was supplied into the furnace interior 1'.

By the measurement of water vapor, the mole number of the water vapor per unit volume (n) was found to be 3.5 mole/m$^3$. The partial pressure of the water vapor was obtained by the formula (5) as $P_w = 0.32$ atm $\approx 240$ mmHg. The dew point $t_w \approx 70°$ C. was obtained from $P_w$ and the data of FIG. 2.

For comparing the obtained dew point with the one obtained by a method, the gases of the furnace interior 1' were sucked outside from the immediate vicinity of the surface 9' and then subjected to measurement of the dew point using a commercially available lithium-chloride dew point meter. The dew point measured by this meter was 71° C.

The dew point measured by the method of the present invention was virtually coincident with the one measured by the conventional method. This fact verified the measurements of the mole concentration and the partial pressure of the water vapor according to the method of the present invention.

EXAMPLE 2

CO gas was measured in this example by using the embodiment shown in FIG. 4.

A black-body radiator furnace having a temperature of 800° C. was used as the light source 4. An interference filter having a wavelength $\lambda$ of 4.6 $\mu$m and a half-width $\Delta\lambda$ of 0.1 $\mu$m was used as the filter 10. An HgCdTe infrared ray sensor was used as the detector 8. CO gas was supplied from a bomb into the furnace interior 1', maintained at a normal temperature, in such an amount that the mole concentration of the CO gas amounted to $n_{CO} = 1.8$ mole/m$^3$.

The mole concentration was measured, using the formula (14), as $n_{CO} = 1.9$ mole/m$^3$, which was close to the supplied mole concentration. The formula (7) was substituted for this value to obtain the partial pressure of the CO gas. $P_{CO} = 0.047$ atm $= 35.7$ mmHg was obtained.

EXAMPLE 3

The measurement devices used in Examples 1 and 2 were fitted to the side walls of a decarburizing-annealing furnace for the production of electrical steel sheets so that the optical path was positioned 10 mm from the sheet surface and crossed perpendicular to the travelling direction of the steel sheet. The average dew point and average CO gas concentration in the vicinity of the sheet surface were continuously monitored for a long time period. The results are shown in FIG. 5.

Figure 5:
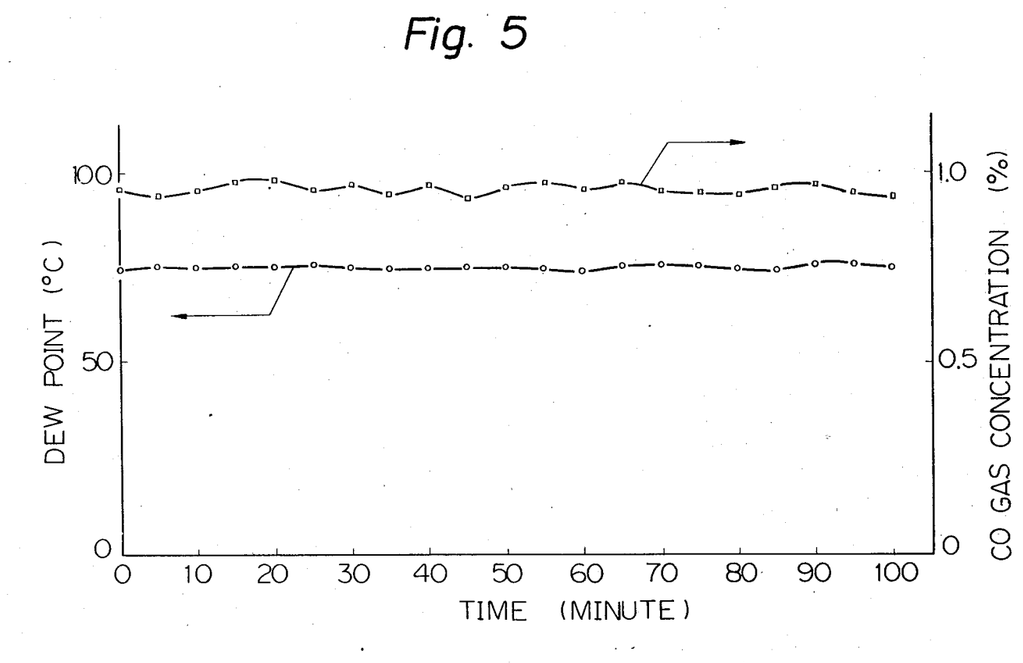
FIG. 5 shows the result of a method according to the present invention for measuring the average dew point and the average CO gas concentration in the vicinity of a steel sheet in a continuous decarburizing-annealing furnace of an electrical steel sheet.

FIG. 5 clearly shows the variation of the average CO gas concentration with time.

As is described hereinabove, particularly in the examples, the concentrations and partial pressures of the water vapor and the CO gas, as well as the partial-pressure ratio measured by the method of the present invention, enable quantitative detection, in situ, of the decarburization reaction occurring on the surface of an electrical steel sheet. During normal production of an electrical steel sheet, such as carried out in Example 3, the variation in the concentration of the CO gas is slight, as shown in FIG. 5. However, when the line speed and/or temperature are changed, any abnormal signal of the CO gas concentration due to such change can be detected by the method of the present invention and can be directly used to control the decarburization process, thereby restoring the process stability.

In addition to the halogen-tungsten lamp and blackbody radiation furnace, other light sources, such as a xenon lamp, a tungsten lamp, and a tunable LASER such as a semiconductor LASER or CO$_2$ LASER, can also be used. Furthermore, a microwave-emitting source can also be used as the light source since wavelength band of the microwave exhibits an absorption property to water vapor and/or CO gas.

The method according to the present invention may be carried out at a plurality of points along the longitudinal direction of a decarburizing-annealing furnace or the travelling direction of a steel sheet so as to accurately detect the progress of decarburization or the interface reaction of an electrical steel sheet.

An emitting source and receptor of an electromagnetic wave can be installed on the furnace walls or outside the furnace, thereby preventing the heat from the furnace interior from influencing the measurement. In this case, continuous measurement is stabilized in every way.

The method according to the present invention not only is used for quantitatively detecting the decarburization reaction of an electrical steel sheet but also can be readily applied for control of the dew point of the furnace interior regarding a radiant-annealing furnace of a stainless steel sheet and continuous annealing of a thin steel sheet.

I claim:

1. A method for quantitatively detecting a decarburization reaction in a decarburization-annealing furnace during the production of an electrical steel sheet, wherein an electromagnetic wave beam, which has a wavelengh exhibiting a characteristic of being absorbed by water vapor and CO gas, is passed across a surface of the electrical steel sheet positioned in said decarburizing-annealing furnace with said passing of said electromagnetic wave beam occurring during said decarburization reaction in said decarburization-annealing furnace and wherein an absorption amount of said passed electromagnetic beam absorbed by the CO gas, which is formed due to a reaction between said water vapor and said surface of the electrical steel sheet during said decarburization reaction, is measured, thereby yielding the average concentrations of said water vapor and said CO gas over said surface, across which said electromagnetic wave passes.

2. A method according to claim 1, wherein a partial pressure of said water vapor and a partial pressure of said CO gas are obtained from said concentrations of water vapor and CO gas, respectively, and, further, a ratio of said partial pressures is obtained.

3. A method for quantitatively detecting a decarburization reaction in a decarburization-annealing furnace during the production of an electrical steel sheet, wherein an electromagnetic wave beam, which has a wavelength exhibiting a characteristic of being absorbed by water vapor and CO gas, is passed across a surface of the electrical steel sheet positioned in said decarburizing-annealing furnace with said passing of said electromagnetic wave beam occurring during said decarburization reaction in said decarburization-annealing furnace and wherein an absorption amount of said passed electromagnetic beam absorbed by the water vapor is measured, thereby yielding the average concentration of said water vapor over said surface, across which said electromagnetic wave beam passes, and then the dew point is obtained from the water vapor concentration.

4. A method according to claim 1, 2, or 3, wherein said electromagnetic wave beam is passed along a width of the electrical steel sheet.

5. A method according to claim 1, 2, or 3, wherein, as an emitting source of the electromagnetic wave beam, one member selected from a group consisting of a lamp for emitting an infrared ray, halogen-tungsten lamp, a xenon lamp, an infrared ray-emitting LASER, a CO2 LASER, and a microwave generator, is used.

6. A method according to claim 1, 2, or 3, wherein an emitting source and a receptor of the electromagnetic beam are installed at side walls of the decarburizing-annealing furnace or outside the decarburizing-annealing furnace.

7. A method according to claim 1, 2, or 3, wherein a plurality of measurement devices of the electromagnetic wave beam are installed in the decarburizing-annealing furnace.

8. A method according to claim 5 wherein said LASER is a semiconductor LASER imitting a variable wavelength infrared ray.

9. A method according to claim 5 wherein said microwave generator is a Gunn diode.

10. A method according to claim 5 wherein said lamp for emitting an infared ray is a black body.

* * * * *

UNITED STATES PATENT AND TRADEMARK OFFICE
CERTIFICATE OF CORRECTION

PATENT NO. : 4,647,319

DATED : March 3, 1987

INVENTOR(S) : T. Iuchi

It is certified that error appears in the above-identified patent and that said Letters Patent is hereby corrected as shown below:

Column 2, line 6, change "$2M_gO.SiO_2$" to --$2M_gO \cdot SiO_2$--.

Column 3, line 15, change "$2FeO.SiO_2$" to --$2FeO \cdot SiO_2$--.

Column 3, line 20, change "$2FeO.SiO_2$" to --$2FeO \cdot SiO_2$--.

Column 6, line 19, change "$-a_w n_w(Z)$ to --$-a_w \cdot n_w \cdot (Z)$--.

Column 6, line 16, change "low" to --law--.

Column 6, line 57, change "$P_w V = N_w R.T$" to --$P_w \cdot V = N_w \cdot R \cdot T$--.

Column 6, line 64, change "$P_w = n_w R.T$" to --$P_w \cdot V = N_w \cdot R \cdot T$--.

UNITED STATES PATENT AND TRADEMARK OFFICE
CERTIFICATE OF CORRECTION

PATENT NO. : 4,647,319

DATED : March 3, 1987

INVENTOR(S) : T. Iuchi

It is certified that error appears in the above-identified patent and that said Letters Patent is hereby corrected as shown below:

Column 7, line 17, change "$P_{CO}=n_{CO}R.T$" to --$P_{CO}=n_{CO} \cdot R \cdot T$--.

Column 7, line 42, change "particulary" to --particularly--.

Column 9, line 13, change "by a method" to --by a conventional method--.

Signed and Sealed this

Twenty-ninth Day of December, 1987

Attest:

DONALD J. QUIGG

Attesting Officer

Commissioner of Patents and Trademarks